United States Patent
Peumans

(10) Patent No.: US 9,528,928 B2
(45) Date of Patent: Dec. 27, 2016

(54) MICROFLUIDICS SYSTEM FOR SEQUENCING

(71) Applicant: IMEC, Leuven (BE)

(72) Inventor: Peter Peumans, Herfelingen (BE)

(73) Assignee: IMEC, Leuven (BE)

( * ) Notice: Subject to any disclaimer, the term of this patent is extended or adjusted under 35 U.S.C. 154(b) by 856 days.

(21) Appl. No.: 13/875,935

(22) Filed: May 2, 2013

(65) Prior Publication Data

US 2013/0296187 A1 Nov. 7, 2013

(30) Foreign Application Priority Data

May 2, 2012 (EP) .................................... 12166484

(51) Int. Cl.

| | | |
|---|---|---|
| *G01N 21/00* | (2006.01) | |
| *G01B 9/02* | (2006.01) | |
| *G02B 6/00* | (2006.01) | |
| *C12M 1/00* | (2006.01) | |
| *C12M 1/34* | (2006.01) | |
| *C12Q 1/68* | (2006.01) | |
| *G01N 21/17* | (2006.01) | |
| *G01N 21/05* | (2006.01) | |
| *G01N 21/39* | (2006.01) | |
| *G01N 21/77* | (2006.01) | |
| *G01N 21/03* | (2006.01) | |

(52) U.S. Cl.
CPC .............. *G01N 21/17* (2013.01); *G01N 21/05* (2013.01); *G01N 21/39* (2013.01); *G01N 21/7703* (2013.01); *G01N 2021/0346* (2013.01)

(58) Field of Classification Search
CPC ..... G01N 21/05; G01N 21/39; G01N 21/7703
USPC ... 356/73.1, 432, 436, 478; 385/12; 435/6.1, 435/283.1, 287.2
See application file for complete search history.

(56) References Cited

U.S. PATENT DOCUMENTS

| | | | |
|---|---|---|---|
| 6,721,053 B1 | 4/2004 | Maseeh | |
| 6,897,959 B2* | 5/2005 | Haensch | ............. G01N 21/255 356/432 |
| 7,796,262 B1 | 9/2010 | Wang et al. | |
| 2002/0047003 A1 | 4/2002 | Bedingham et al. | |
| 2002/0068018 A1 | 6/2002 | Pepper et al. | |
| 2005/0035278 A1 | 2/2005 | Margalit et al. | |
| 2008/0165355 A1 | 7/2008 | Yasui et al. | |
| 2010/0248391 A1 | 9/2010 | Garcia Tello | |
| 2011/0149285 A1* | 6/2011 | Chen | .................. G01N 21/7746 356/432 |

FOREIGN PATENT DOCUMENTS

| | | |
|---|---|---|
| EP | 2270478 A1 | 1/2011 |
| WO | 2006/117541 A1 | 11/2006 |

OTHER PUBLICATIONS

European Search Report, European Patent Application No. 12166484.1 dated Oct. 5, 2012.
Michaud-Belleau, Vincent et al., "Whipering Gallery Mode Sensing With a Dual Frequency Comb Probe", Optics Express, vol. 20, No. 3, Jan. 25, 2012, pp. 3066-3075.

* cited by examiner

*Primary Examiner* — Narayan Bhat
(74) *Attorney, Agent, or Firm* — McDonnell Boehnen Hulbert & Berghoff LLP

(57) ABSTRACT

A sensor chip for use in multiplexed analysis of at least one sample is described. The sensor chip comprises a plurality of sensing sites, each sensing site adapted for sensing an optional interaction of a sample with a component and an input waveguide for receiving radiation from a frequency comb radiation source and guiding said radiation along said plurality of sensing sites. At each sensing site, a distinct optical sensitive element is adapted for, at a distinct frequency, sensing an optional interaction of said sample with said component. An output means provides output of the radiation representative for the sensing dependent on said optional interaction of said sample with said component at said plurality of sensing sites.

15 Claims, 4 Drawing Sheets

MICROFLUIDICS SYSTEM FOR SEQUENCING

CROSS-REFERENCE TO RELATED APPLICATIONS

This claims the benefit of priority of European Patent Application no. 12166484.1, filed May 2, 2012, which is hereby incorporated herein by reference in its entirety.

BACKGROUND OF THE INVENTION

Field of the invention

The invention relates to the field of sensing such as for example biosensing. More particularly, the present invention relates to methods and systems for multiplexed, i.e. simultaneous, optical sensing or characterizing samples, such as for example used in sequencing applications.

Background of the Invention

For a number of sensing applications, such as for example different biosensing applications, the need for multiplexed processing is high. In several applications, a large number of sensing events needs to be performed for obtaining an accurate characterization of a sample. One example of such an application whereby a large number of sensing events are required is sequencing, although also other applications benefit from multiplexed sensing. To obtain sufficiently efficient characterisation systems, there is a constant pressure from the market for increasing the number of sensing events that can be obtained with a microfluidic chip per day. In order to increase this number, the number of sensing sites can be increased. The density of sensing sites that can be introduced on a microfluidic chip can be high, e.g. more than $10^4$, more than $10^5$, more than $10^6$, . . . .

Whereas in principle it would be possible to provide a separate sensor for each of the sensing sites, this would not result in a practical solution, especially not when a large density of sensing sites is used. Consequently, sensing techniques are preferred that allow multiplexed sensing based on the same measurement. Different measurement techniques that have been used in the past are fluorescence based imaging, chemiluminescence imaging, electrical measurements, optical detection making use of white light sources or tunable lasers, etc.

Although a number of different detection techniques have already been suggested for improving multiplexed detecting, further improvement is needed if high speed processing, e.g. at a rate of at least 100 Gbp/day or even better at a rate of at least 300 Gbp/day, is to be obtained.

SUMMARY OF THE INVENTION

It is an object of embodiments of the present invention to provide a detection device, e.g. a biosensing device, allowing efficient multiplexed sensing or characterizing.

It is an advantage of embodiments of the present invention that a biosensor with a high throughput can be obtained.
It is an advantage of embodiments of the present invention that use can be made of a single light source.
It is an advantage of embodiments of the present invention that use can be made of a parallelized integrated detection system that is fully compatible with a semiconductor platform such as the silicon photonics platform.
It is an advantage of embodiments of the present invention that use can be made of off-the-shelf optical instrumentation, avoiding expensive optical solutions.

It is an advantage of embodiments of the present invention that read-out can be performed in the Fourier-domain, allowing in easy multiplexed detection.

It is an advantage of embodiments of the present invention that by using a radiation source being a frequency comb, multiplexing for a large number of sensing sites can be performed.

The present invention relates to a sensor chip for use in multiplexed analysis of at least one sample, the sensor chip comprising a plurality of sensing sites, each sensing site adapted for sensing an optional interaction of a sample with a component, an input waveguide for receiving radiation from a frequency comb radiation source and guiding said radiation along said plurality of sensing sites, at each sensing site, a distinct optical sensitive element adapted for, at a distinct frequency of said radiation, sensing the optional interaction of said sample with said component, whereby the distinct frequency for said sensing is different for each sensing site, an output means for outputting radiation representative for said sensing dependent on said optional interaction of said sample with said component at said plurality of sensing sites. It is an advantage of embodiments of the present invention that, using a single source, a plurality of analysis can be performed in an efficient manner.

The distinct optical sensitive element may be a distinct optical resonator element adapted for at a distinct frequency of said radiation, resonant radiation coupling, e.g. efficient radiation coupling, between the input waveguide and the optical resonator element, the resonant radiation coupling being dependent on the optional interaction of the sample with the component, whereby the distinct frequency for the resonant radiation coupling is different for each sensing site, and wherein the output means may be adapted for outputting radiation representative for the resonant radiation coupling.

The optical resonator element may be a ring resonator.
The ring resonator may be a micro ring resonator.

It is an advantage of embodiments according to the present invention that the components can be easily implemented in a semiconductor platform, such as for example a silicon photonics platform.

The input waveguide and the optical sensitive elements may be positioned for side resonant coupling.

Each of the optical sensitive elements may be adapted in size or in environment for inducing a distinct frequency for said resonant radiation coupling with the input guide. Parameters that may be used are ring diameter, e.g. if each ring resonator is tuned for a specific wavelength, or e.g. distance from the waveguide. In some embodiments the coupling should be weak enough to ensure equal power delivery to all sensing elements from the same waveguide. It is an advantage of embodiments according to the present invention, that tuning the different optical resonator elements can easily done during manufacturing by functionalizing a surface of or near the optical resonators or by designing the optical resonator elements, e.g. by selecting a different radius in case ring resonators are used.

The input waveguide may be a branched input waveguide for guiding said radiation along said plurality of sensing sites. The branched input waveguide may also be referred to as a tree-like waveguide.

The output means may be a waveguide being part of the same waveguide as the input waveguide or being in direct optical connection therewith.

The output means may be an output waveguide, distinct from the input waveguide, and positioned with respect to said optical resonator elements so as to allow resonant optical coupling.

The output means may be a set of output waveguides, distinct from the input waveguide, and positioned with respect to said optical resonator elements so as to allow resonant optical coupling each of said output waveguide outputting radiation corresponding with one of the distinct frequencies.

The present invention also relates to a sensor chip reader for reading a sensor chip as described above, wherein the sensor chip reader comprises an optical radiation source being a frequency comb radiation source, and a radiation guiding means for guiding the radiation to an input guiding means of the sensor chip.

The sensor chip reader furthermore may comprise a detector for detecting radiation representative for resonant radiation coupling dependent on said optional interaction of said sample with said component at said plurality of sensing sites in the sensor chip.

The detector may be adapted for detecting the radiation representative for resonant radiation coupling dependent on the optical interaction of the sample with the component for each sensing site in a distinct detection channel.

The optical radiation source may comprise a mode-locked laser providing frequency comb radiation in one or more of the infrared, visible or ultraviolet spectral range.

The present invention also relates to a method for performing multiplexed analysis of samples, the method comprising, guiding frequency comb radiation simultaneously to a plurality of sensing sites, each sensing site adapted for sensing an optional interaction of a sample with a component, for each of the sensing sites, allowing at a distinct frequency sensing the optional interaction of said sample with said component in or near the optical sensitive element, and outputting radiation representative for said sensing dependent on the optional interaction of said sample with said component at said plurality of sensing sites.

The method furthermore may comprise, based on spectral analysis of said outputted radiation, deriving for each of the plurality of the sensing sites whether or not an interaction of the sample with the component occurred.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
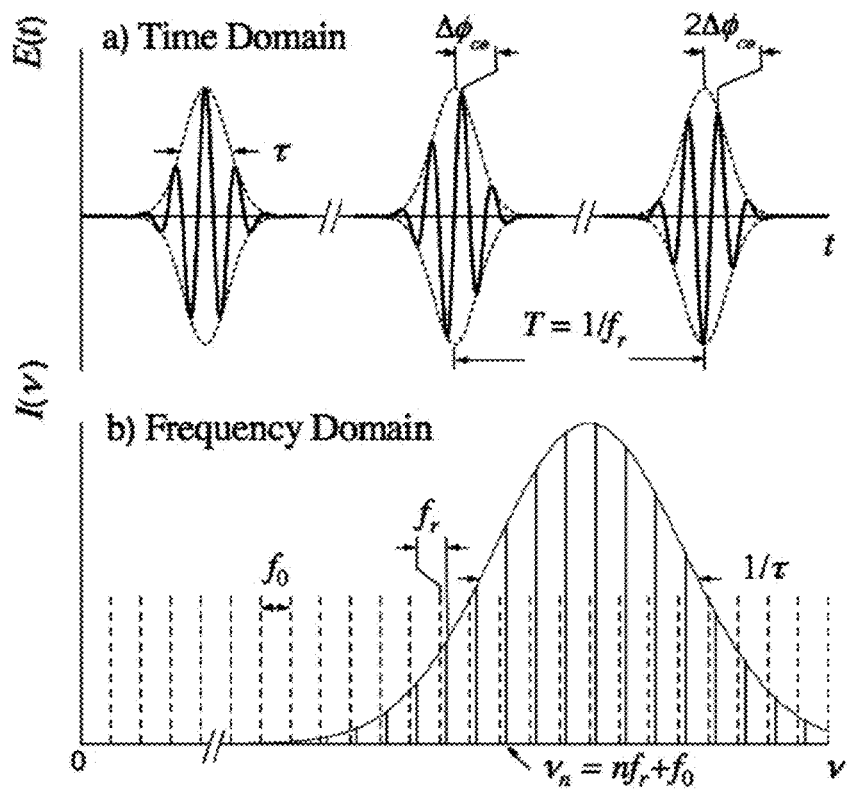
FIG. 1 illustrates the principle of frequency comb radiation, as can be used in embodiments according to the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to a radiation source, reference is made to a source adapted for providing any type of electromagnetic radiation, such as for example infrared radiation, near infrared, visible radiation, ultraviolet radiation, etc. The radiation source may be selected and arranged such that losses are as small as possible.

Where in embodiments of the present invention reference is made to a sensor chip, reference may be made to a device wherein measurements can be performed on samples. Such a sensor chip may be a cartridge that can be used in a reader system for performing the sensing. It may be disposable, limited re-usable or re-usable.

In a first aspect, the present invention relates to a sensor chip for use in a system for multiplexed analyzing of samples based on optical detection. It thereby is an advantage of embodiments of the present invention that the sensor chip can provide a large number of measurements sites, as this results in an efficient multiplexing device. In at least some embodiments of the present invention, the number of read locations can be $10^6$ or higher, although embodiments of the present invention are not limited thereby. The sensor chip may for example be especially suitable for performing sequencing, such as sequencing by synthesis. For such applications, the sample or component delivery and the washing steps may be performed based on microfluidic channels, although embodiments of the present invention are not limited thereto. It is an advantage of at least some embodiments of the present invention, that the suggested detection techniques can be easily combined with microfluidic devices. According to embodiments of the present invention, the a sensor chip is provided that comprises a plurality of sensing sites, each sensing site adapted for sensing an optional interaction of a sample with a component. Such adaptation may be performed in a plurality of ways, e.g. by providing a functionalized surface in or near the sensing site and allow interaction of the a sample to be tested with reagents, e.g. predetermined components, for detecting an interaction such as for example a binding. A sensor device according to embodiments of the present invention comprises an input waveguide for receiving radiation from a frequency comb radiation source. The input waveguide is adapted for guiding the frequency comb radiation along the plurality of sensing sites. The input waveguide may therefore be a branched input waveguide, also referred to as a tree-like waveguide, for distributing the radiation along a pathway, advantageously a short pathway, to the sensing sites of interest. The frequency comb radiation source may be obtained by mode locking of laser pulses using a lasing device. The principle of frequency comb radiation is illustrated with reference to FIG. 1. In a lasing device, certain frequencies of the electromagnetic radiation have exactly the right wavelengths in the laser cavity to resonate and form standing waves. The pulsed laser typically emits brief pulses in the time domain, as illustrated in the upper graph of FIG. 1. Such brief pulses are made up of a multiple frequencies. The lower graph of FIG. 1 illustrates the resulting output in the frequency domain. The intensities obtained typically are not equal for all emitted frequencies, rather an envelope peak shape can be defined indicative of the intensities that are emitted. The latter can also be seen in the lower graph of FIG. 1. Further according to embodiments of the present invention, at each sensing site, a distinct optical sensing element is provided that is adapted for, at a distinct frequency of the frequency comb radiation, sensing dependent on the optional interaction of the sample with the component. In a preferred set of embodiments, at each sensing site, a distinct optical resonator element is provided that is adapted for, at a distinct frequency of the frequency comb radiation, resonant radiation coupling between the input waveguide and the optical resonator element. The resonant radiation coupling thereby is dependent on the optional interaction of the sample with said component. The latter can e.g. be obtained by the interaction of the sample and the component resulting in a change in the refractive index of the optical resonator element. By making sure that the distinct frequency for sensing, e.g. by resonant radiation coupling, is different for each sensing site, effects of interaction at the different sensing sites can be distinguished from each other. The sensor chip also comprises an output means for outputting radiation representative for the sensing, e.g. said resonant radiation coupling, dependent on said optional interaction of said sample with said component at said plurality of sensing sites, so that the effects of optional interaction for the different sensing sites can be distinctively studied.

Figure 2A:
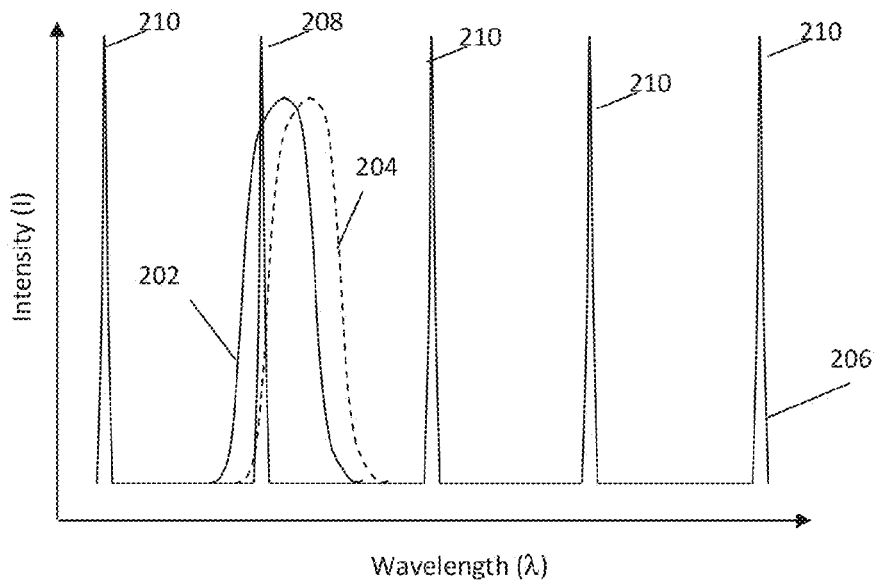
FIG. 2A and FIG. 2B illustrate the principle of detection based on resonant coupling making use of frequency comb radiation, as used in embodiments according to the present invention.
Figure 2B:
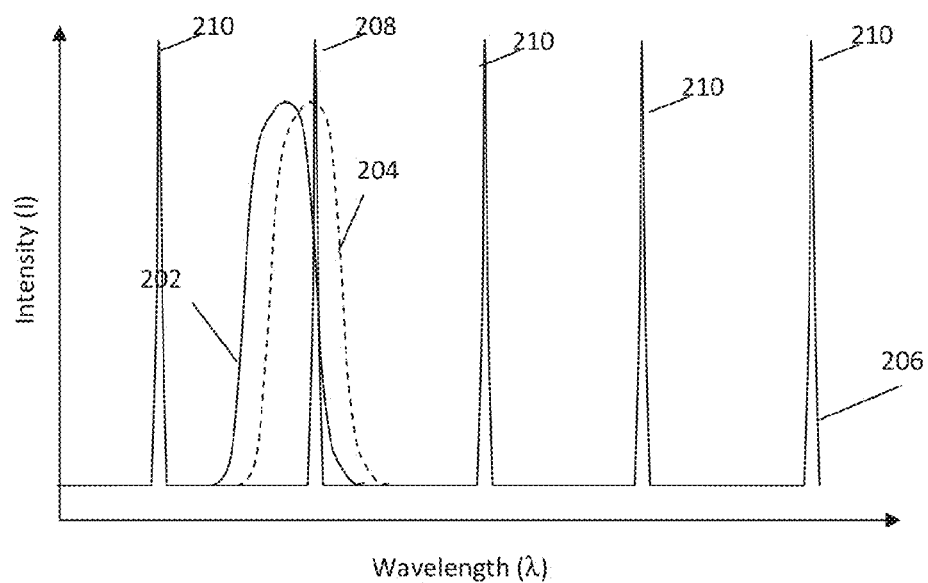
Figure 3:
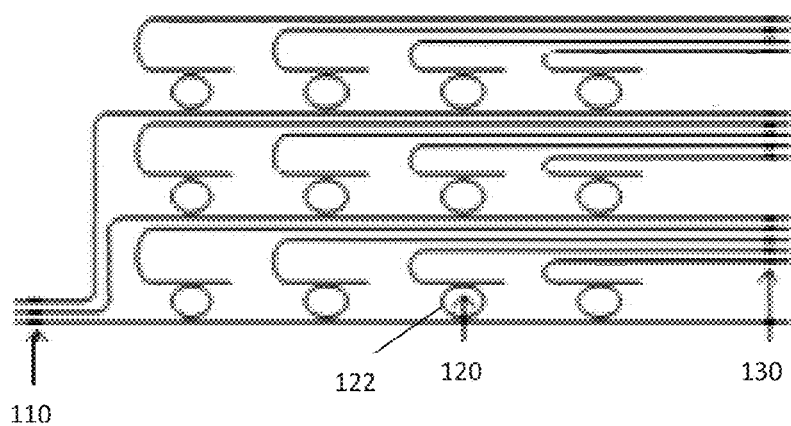
FIG. 3 illustrates part of a sensor chip based on the detection principle of resonant coupling making use of a frequency comb radiation, according to an embodiment of the present invention.
Figure 4:
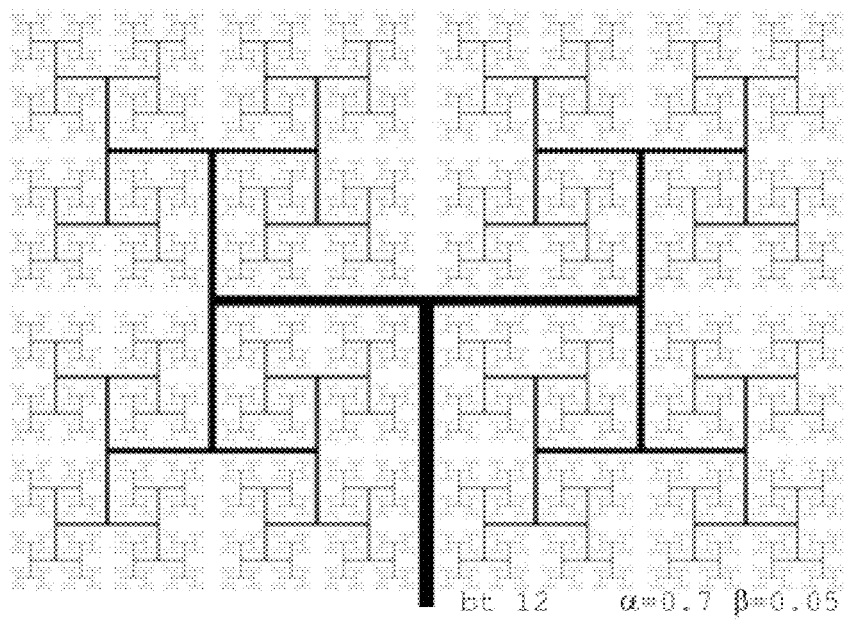
FIG. 4 illustrates an example of an branched input waveguide as can be used in a sensor chip according to an embodiment of the present invention.

By way of illustration, embodiments of the present invention not being limited thereto, an exemplary sensor chip, according to an embodiment of the present invention, will be further discussed below, illustrating standard and optional features of embodiments of the present invention. The example will be illustrated for optical resonant elements, but other sensing techniques also can be used, without departing from the scope of embodiments of the present invention. Reference will be made to FIG. 2 to FIG. 4.

The sensor chip 100, of which a part is schematically represented in FIG. 3, comprise an input means 110 for receiving frequency comb radiation and for guiding the radiation to the different sensing sites. The input means 110 typically may be an input waveguide, whereby the input waveguide could be a linear waveguide passing all sensing sites, but advantageously is branched waveguide, also referred to as tree-like waveguide, for delivery of the frequency comb radiation to the different sites. In FIG. 3, the input means 110 shown comprises three branches, each delivering input to different sensing sites 120. One example of a branched like input waveguide 110 for delivery of the frequency comb radiation is shown in FIG. 4, illustrating that the input waveguide 110 splits in a plurality of branches, and that a number of branching levels are provided. Such a branched waveguide 110 may assist in reducing the optical pathlength that the frequency comb radiation has to travel, e.g. compared to a single waveguide channel subsequently passing all sensing sites.

By way of illustration, the schematic representation in FIG. 3 also illustrates a few of the plurality of sensing sites 120 where sensing can occur. Advantageously, according to embodiments of the present invention, the sensor chip 100 comprises a large number of sensing sites 120. The number of sensing sites may be at least $5.10^5$, advantageously at least $1.10^6$. The latter provides the possibility to perform multiplexing at large scale. Especially for example in sequencing by synthesis, such multiplexing is required for obtaining the necessary efficiency. According to embodiments of the present invention, the sensing or detection principle is, at each sensing site, based on resonant radiation coupling between an input means 110 and an optical resonator element 122. The optical resonator element 122 may be any type of optical resonator element such as for example a ring resonator, a linear cavity resonator, a photonic crystal resonator, . . . . The optical resonator element 122 may be an optical structure that is sensitive to local changes in refractive index.

Figure 5:
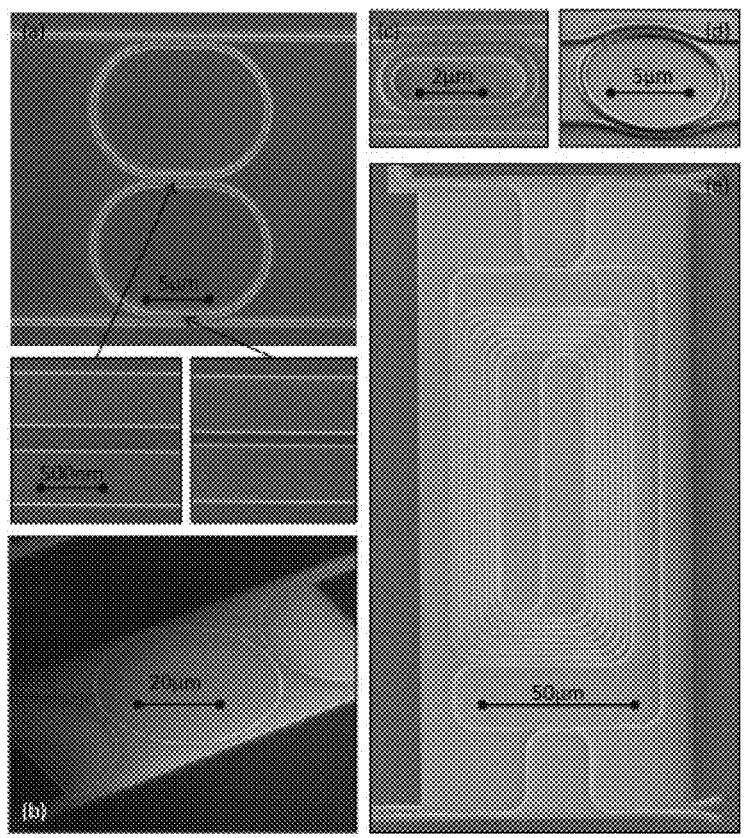
FIG. 5 illustrates possible resonating optical elements as can be used in a sensor chip according to an embodiment of the present invention.
Figure 6:
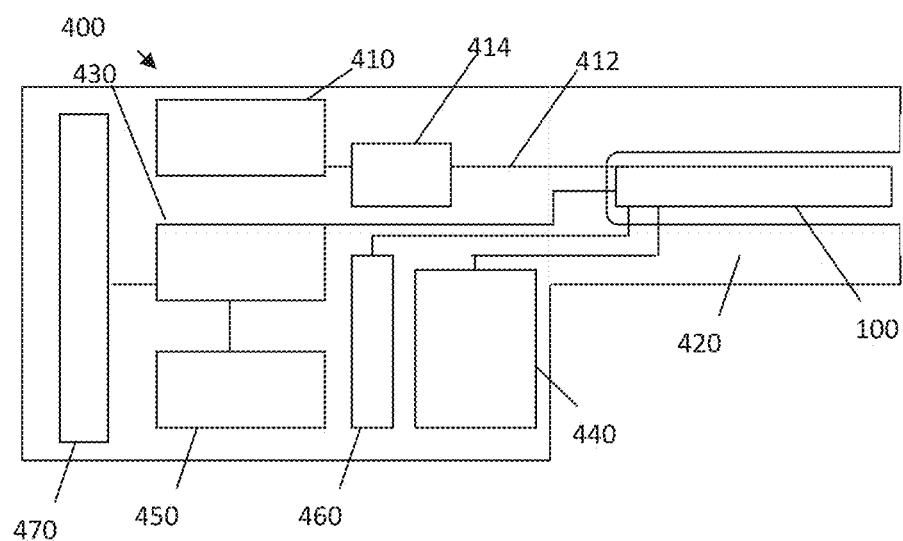
FIG. 6 illustrates a sensor chip reader comprising a frequency comb radiation source according to an embodiment of the present invention.

By way of illustration, embodiments of the present invention not being limited thereto, some examples of resonator structures that can be used are shown in FIG. 5, illustrating a double ring structure in part (a), a ring shaped resonator structure in part (b), a racetrack or elliptically shaped resonator structure in parts (c) and (d) and a folded resonator structure in part (e) of FIG. 5. An optical resonator element 122 typically is characterized by a given resonance frequency, i.e. it can support radiation having a particular frequency, referred to as the resonance frequency. The resonance frequency typically depends on the refractive index and geometrical properties of the optical resonator element 122. For detection purposes use is made of the fact that when, in, on or in the neighbourhood of the optical resonator element 122 an interaction between a sample and a component occurs, e.g. binding of a component to the sample or to a specific part thereof, this will influence the refractive index and consequently will influence the resonance frequency. The latter is also illustrated in FIG. 2, wherein the resonance peak 202 is shown when no interaction between the sample and the component has taken place (indicated by the full line resonance peak), and wherein the resonance peak 204 illustrates the situation wherein interaction between the sample and the component has taken place, resulting in a shifted resonance frequency (indicated by the dashed resonance peak). According to embodiments of the present invention, the optical resonator element is adapted for resonant radiation coupling between the input means and the optical resonator element. The latter can e.g. be obtained as follows. As indicated above the input means 110 guides the frequency comb radiation along the sensing sites, more particularly, along the optical resonator elements in the sensing sites, such that if the frequency comb radiation comprises a frequency corresponding with the resonance frequency of the optical resonator element, optical coupling can occur. According to embodiments of the present invention, for each of the sensing sites, the optical resonator element is selected (in environment and geometrical shape), such that its resonance frequency substantially corresponds with a distinct frequency component of the frequency comb radiation. In other words, the optical resonator elements are tuned to all correspond with a distinct—different—frequency component of the frequency comb radiation used in the sensing system. As illustrated in FIG. 2A, the resonance peak 202 substantially corresponds with one frequency component 208 of the frequency comb radiation 206 but not with other frequency components 210 thereof. In this way, by analyzing that frequency component in a corresponding output radiation signal, it is possible to obtain information from the particular sensing site corresponding with that frequency component.

As indicated above, the resonant radiation coupling between said input waveguide and said optical resonator element may be dependent on said optional interaction of said sample with said component. For example, the following two situations may occur:

The resonance frequency of the optical resonator element has been selected such that, when no interaction between the sample and the component occurs, the match between the resonance frequency and the frequency component of the frequency comb radiation is largest, resulting in the highest coupling of radiation from the input means to the resonator. In this interaction between the sample and the component, e.g. by binding will result in a reduction of the coupling efficiency to the resonator, due to the shift of the resonance frequency away from the frequency component in the frequency comb radiation. The latter corresponds with the situation as shown in FIG. 2A.

The resonance frequency of the optical resonator element still substantially corresponds with the frequency component of the frequency comb radiation, but it is selected such that the optimum resonance frequency does not coincide with the frequency component of the frequency comb radiation when no interaction between the sample and the component occurs and so that the optimum resonance frequency shifts towards the optimum frequency of the frequency component of the frequency comb radiation when interaction between the sample and the component occurs. In this way, the coupling efficiency between the input means 110 and the resonator 122 will increase upon interaction between the sample and the component. The latter corresponds with the situation as shown in FIG. 2B.

According to embodiments of the present invention, the sensor chip 100 also comprises an output means 130 for outputting radiation representative for said resonant radiation coupling dependent on said optional interaction of said sample with said component at said plurality of sensing sites. Different options can therefore be used. In one embodiment for example, the output means 130 is an output waveguide being part of the input waveguide or being directly connected thereto. The intensity of the radiation in this waveguide will depend on the amount of coupling that occurred between the input waveguide 110 and the optical resonator element 120, and thus will be an indication whether interaction occurred between the sample and the component. Consequently, the interaction can be sensed.

In another embodiment, the output means 130 is distinct from the input means 110. It may in a particular example be a single output waveguide passing along all optical resonator elements, whereby the radiation coupled from the input means to the optical resonators, is coupled to the output waveguide. In this way a single output radiation signal is obtained, whereby analysis of the different sensing sites can be performed by spectral analysis of the single output radiation signal.

In another particular embodiment, the output means 130 may comprise a plurality of output waveguides, each output waveguide passing along a specific optical resonator element 122, whereby the radiation coupled from the input means 110 to the particular optical resonator 122, is coupled to the particular output waveguide. The output signal is then a set of output signals, each being representative for an interaction site, which can be processed separately, e.g. by directing the different output waveguides to distinct pixels of a detector. Alternatively, the output signals can also be coupled, e.g. through a coupler towards a common exit waveguide, and the resulting signal can be separated thereafter, e.g. outside the sensor chip 100, by spectral processing of the signal. In still another particular embodiment, the output signals may be grouped into several output waveguides, thus combining features of the above described embodiments.

For the sake of completeness, it is noticed that also other components may be present in the sensor chip 100. The sensor chip may for example comprise at each of the sensing sites, an interaction surface, where e.g. the sample to be studied can be positioned or where a reagent component with which interaction is to be measured can be positioned. Typically such an interaction surface will be in the vicinity of the optical resonator element, as the influence of the interaction is to be felt by the optical resonator element, typically by its refractive index being altered.

The sensor chip 100 also may comprise means for bringing the sample or the reaction components towards interaction surface for optionally inducing an interaction. In some embodiments, such means for transporting sample or reaction components may be a set of microfluidic channels. Further typical components of the chip may be the presence of a waste channel, wherein the remaining fluid can be transported after interaction, valves, etc. In one example, the waste channel is adapted with a first output through which the used fluid can be outputted. The latter can be performed in a spontaneous or a in a forced manner. Removal of the fluid may for example be performed by forcing the fluid out of the microfluidic chip. In one example this may for example be performed by pumping, e.g. inducing a negative pressure at the output side or inducing a positive pressure at the input side. In one example, the waste channel may be adapted with an opening through which the negative pressure can be induced. Typically, a pumping means or forcing means will not be part of the microfluidic chip, but rather be part of a sensing system or reader.

Other features and components, known to the person skilled in the art, also may be present.

It is an advantage of at least some embodiments of the present invention that the sensor chip can be fully manufactured (e.g. both microfluidic components and sensing components present in the chip) using one type of technology, e.g. using silicon-photonics based technology, although embodiments are not limited thereto. Furthermore, it is an advantage of at least some embodiments of the present invention that existing manufacturing technology can be used for manufacturing the above described sensor chip.

According to one aspect, the present invention relates to a sensor system 400, sometimes also referred to as a chip reader, for co-operating with a sensor chip 100 as described in the first aspect. The sensor system 400 according to embodiments of the present invention comprises an optical radiation source 410 being a frequency comb radiation source and optionally also a radiation guiding means 412 for guiding the radiation to an input means of the sensor chip 100. Alternatively, the optical radiation may directly irradiate the input means of the sensor chip 100.

The frequency comb radiation source 410 may be based on a lasing device. By way of illustration, embodiments of the present invention not being limited thereto, some possible features of lasing devices that may be used are the possibility for providing modelocking, a repetition rate between 100 MHz and 40 GHz, e.g. between 5 GHz and 20 GHz, a pulse length in a picoseconds range, advantageously below 1 ps, a narrow bandwidth, a small comb spacing, a high output power, a large number of spectral lines, etc. The frequency comb radiation may further be a radiation input processing element 414, such as a filter element or pulse compressor. In one embodiment, the system comprises a pulse compressor, which may be based on standard pulse compressor technology, for increasing the number of spectral lines and for reducing the pulse length.

The sensor system also may comprise a chip holding means 420 for holding the chip 100 in a predetermined manner, so that optionally accurate connection with e.g. fluidic supplies to and from the sensor chip, ports for inducing a pressure in the chip, electrical contacts, optical connections, etc. can be obtained. In some embodiments, the sensor system may be adapted for receiving the sensor chip in a slot.

The sensor system also may comprise a detector 430 for detecting radiation representative for sensing, e.g. by a varying resonant radiation coupling, dependent on said optional interaction of said sample with said component at said plurality of sensing sites in the sensor chip. Such a detector may be adapted for receiving information from the different sensing sites separately by a plurality of output waveguides on the chip 100, coupling information of the different sensing sites to separate pixels of the detector. Alternatively, the detector also may be adapted for receiving all information as a single signal having a spectral dependency. The detector may then be equipped with or communicate with a processor for spectrally processing the measured results for obtaining information about the individual sensing sites. One example of a detector that can be used could be an InGaAs linescan camera, allowing fast detection. A 2D array imager (conventional image sensor) can also be used in combination with visible light, resulting in cheaper components.

The sensor system 400 also may comprise a fluidic storage and transportation means 440 for supply and removal of fluidics to the sensor chip. Other optional components related thereto may be a pumping means for transporting the fluid, or valves, also for transporting the fluid. The system also advantageously comprises a processor 450 for processing the data registered with the detector. Such a processor 450 may be incorporated in the sensor or alternatively can be separate therefrom, e.g. not being part of the sensor system 400. Control sensors 460, e.g. for controlling accurate flow in the sensor chip, for controlling temperature in the sensor chip, . . . also may be included.

The sensor 400 advantageously comprises a controller 470. Such a controller may for example be used for controlling and timing the sensing e.g. by controlling the radiation source and the detector in case optical sensing is performed, etc.

In another aspect, the present invention relates to a method for performing multiplexed analysis of samples. The method typically comprises guiding frequency comb radiation simultaneously to a plurality of sensing sites, each sensing site adapted for sensing an optional interaction of a sample with a component. The method also comprises, for each of the sensing sites, allowing—at a distinct frequency—resonant coupling of the frequency comb radiation to an optical resonator element, said resonant radiation coupling being dependent on said optional interaction of said sample with said component in or near the optical resonator element, and outputting radiation representative for said resonant radiation coupling dependent on said optional interaction of said sample with said component at said plurality of sensing sites. The method may furthermore comprise, based on spectral analysis of said outputted radiation, for each of the plurality of the sensing sites deriving whether or not an interaction of the sample with the component occurred. Other features and advantages of method embodiments of the present invention may express the functionality of components described in the first or second aspect.

The invention claimed is:

1. A sensor system for use in multiplexed analysis of at least one sample, the sensor system comprising a sensor chip and a sensor chip reader operatively coupled to the sensor chip, the sensor chip reader comprising:
    an optical radiation source being a frequency comb radiation source configured to provide frequency comb radiation of a plurality of distinct frequencies, and
    a radiation guide,
    the sensor chip comprising
    a first plurality of sensing sites, each sensing site configured to sense interaction of a sample with a component,
    an input waveguide configured to receive radiation from the frequency comb radiation source and guide said radiation along said plurality of sensing sites, the radiation guide of the sensor chip reader being configured to optically couple the optical radiation source to the input waveguide of the sensor chip,
    at each sensing site of the first plurality of sensing sites, a distinct optical sensitive element configured to, at a single distinct frequency of said frequency comb radiation, sense the interaction of said sample with said component, wherein the single distinct frequency for said sensing is different for each sensing site of the first plurality of sensing sites,
    an output configured to output radiation at said distinct frequencies representative for said sensing dependent on said interaction of said sample with said component at said first plurality of sensing sites.

2. A sensor system according to claim 1, wherein the distinct optical sensitive element is a distinct optical resonator element configured to provide, at a distinct frequency of said radiation, resonant radiation coupling between the input waveguide and the optical resonator element, the resonant radiation coupling being dependent on the interaction of the sample with the component, whereby the distinct frequency for the resonant radiation coupling is different for each sensing site, and wherein the output is configured to output radiation representative for the resonant radiation coupling.

3. A sensor system according to claim 2, wherein said optical resonator element is a ring resonator.

4. A sensor system according to claim 1, wherein the input waveguide and the optical sensitive elements are positioned for side resonant coupling.

5. A sensor system according to claim 1, wherein each of the optical sensitive elements is configured via size or environment with a functionalized surface or near the optical sensitive elements to induce a distinct frequency for said resonant radiation coupling with the input waveguide.

6. A sensor system according to claim 1, wherein said input waveguide is a branched input waveguide configured to guide said radiation along said plurality of sensing sites.

7. A sensor system according to claim 1, wherein said output is a waveguide being part of the same waveguide as the input waveguide or being in direct optical connection therewith.

8. A sensor system according to claim 1, wherein said output is an output waveguide, distinct from the input waveguide, and positioned with respect to said optical resonator elements so as to allow resonant optical coupling.

9. A sensor system according to claim 1, wherein said output is a set of output waveguides, distinct from the input waveguide, and positioned with respect to said optical resonator elements so as to allow resonant optical coupling each of said output waveguide outputting radiation corresponding with one of the distinct frequencies.

10. A sensor system according to claim 1, wherein the sensor chip reader further comprises a detector configured to detect radiation representative for resonant radiation coupling dependent on said interaction of said sample with said component at said plurality of sensing sites in the sensor chip.

11. A sensor system according to claim 10, wherein the detector is configured to detect the radiation representative for resonant radiation coupling dependent on the optical interaction of the sample with the component for each sensing site in a distinct detection channel.

12. A sensor system according to claim 1, wherein the optical radiation source comprises a mode-locked laser providing frequency comb radiation in one or more spectral ranges selected from infrared, visible and ultraviolet.

13. A sensor system according to claim 1, further comprising a chip holder in which the sensor chip is disposed.

14. A method for performing multiplexed analysis of samples, the method comprising,
    providing a sensor system according to claim 1,
    guiding frequency comb radiation simultaneously to a plurality of the sensing sites,
    for each of the sensing sites, allowing at a distinct frequency sensing the interaction of said sample with said component in or near the optical sensitive element, and
    outputting radiation at said distinct frequencies representative for said sensing dependent on the optional interaction of said sample with said component at said plurality of sensing sites.

15. A method according to claim 14, the method further comprising, based on spectral analysis of said outputted radiation, deriving for each of the plurality of the sensing sites whether or not an interaction of the sample with the component occurred.

* * * * *